United States Patent [19]

Wright

[11] 4,074,712
[45] Feb. 21, 1978

[54] PROPHYLACTIC ARTICLE

[76] Inventor: A. Francis Wright, 25961 Highland Road, Richmond Heights, Ohio 44143

[21] Appl. No.: 727,270

[22] Filed: Sept. 27, 1976

[51] Int. Cl.² .............................................. A61F 5/00
[52] U.S. Cl. ....................................... 128/79; 128/294
[58] Field of Search .............. 128/79, 294, 157, 132 R

[56] References Cited
U.S. PATENT DOCUMENTS

| 713,900 | 11/1902 | Miller et al. | 128/294 |
| 3,648,700 | 3/1972 | Warner | 128/294 |

FOREIGN PATENT DOCUMENTS

| 146,306 | 6/1936 | Austria | 128/294 |
| 2,020,280 | 11/1971 | Germany | 128/294 |

Primary Examiner—Lawrence W. Trapp
Attorney, Agent, or Firm—Frank B. Robb

[57] ABSTRACT

A prophylactic article having a body of thin tubular form, and a generally hemispherical cap spaced therefrom, with the opening toward one end of the body, strap-like elements connect the body and cap in the relationship described, and are of such proportions as to provide the maximum open area between the body and cap.

3 Claims, 2 Drawing Figures

PROPHYLACTIC ARTICLE

OBJECTS OF THE INVENTION

It is a principal object of this invention to provide a prophylactic article of novel construction in that it is essentially comprised of two spaced parts connected in a manner to provide the contraceptive function, yet not interfere with the physical reaction as is the case with the usual article presently available.

Another object hereof is to provide an article of the class described, wherein the same is composed of the usual flexible membrane material for the body, a cap of similar material and strap-like elements connecting the same to maintain the position and relationship whilst providing the maximum open area therebetween.

Other and further objects of the invention will be understood from the specification herein, and disclosed in the drawing, wherein.

DESCRIPTION OF THE INVENTION

Figure 1:
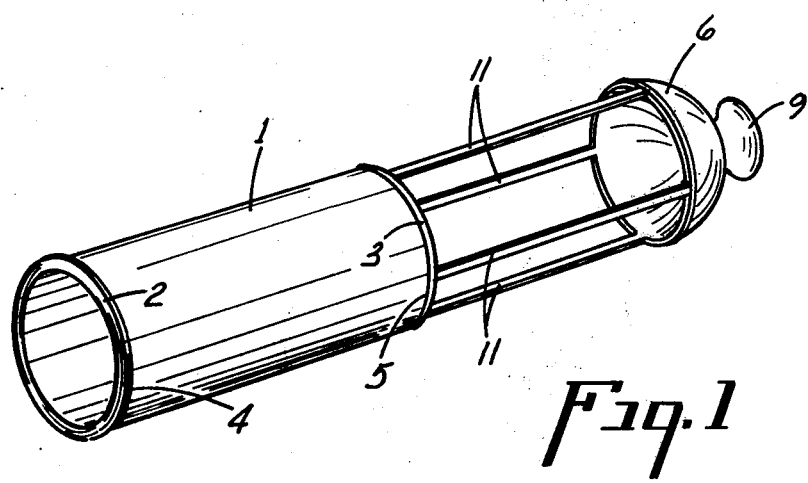
FIG. 1 is a perspective view of the article hereof.

Referring to FIG. 1, the article is shown as comprising a tubular body 1, made of the usual membrane material such as latex or the like, having the reinforcing ribs 2 and 3 at the respective ends 4 and 5, these being open and the body being of any preferred length, and stretchable lengthwise and diametrically.

Figure 2:
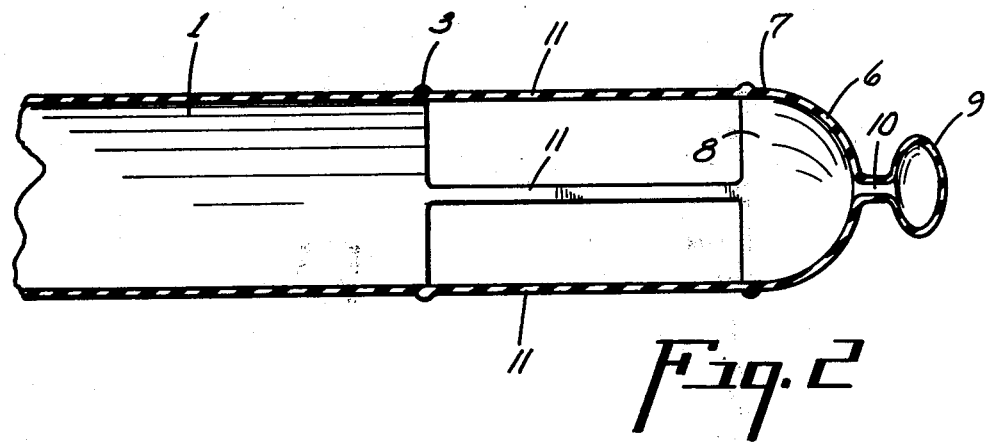
FIG. 2 is a fragmentary sectional view, illustrating the article in further detail.

Spaced from the body 1 is the cap 6 shown in sectional detail in FIG. 2 as comprising a hemispherical member with a reinforcing rib 7 at the open end 8 thereof.

The cap 6 may be provided with a reservoir 9 of suitable size, and proportion, and integral with the cap as shown, being connected thereto by the passage 10, the cap and reservoir being of like material to that of the body 1.

The cap 6 and body 1 are connected by strap-like elements such as 11, of relatively thin form and of sufficient length to provide an open area of adequate size to substantially expose the glans of the user and thus retain the sensitivity sought to be provided hereby since virtually none of the same will be covered though the cap will serve as a means to position a reservoir as shown. The material from which the cap 6 is formed, will be of the usual and flexible form to provide a reservoir itself even without the portion 9 separately formed as shown.

The cap 6, body 1 and reservoir 9, if provided, as well as the elements 11, will be molded as a single article in the manufacture thereof, and of any suitable sanitary material, and in any preferred manner whereby the same will be able to be packaged and sold in the customary way.

It should be understood that the manner of connection of the cap 6 with the body 1 is such as to provide the greatest amount of open area, whether the said connection be by the straps or like elements 11, or in some other way such as by lattice work or the like.

It is emphasized that the important aspect of this connection is such that the open area is as great as possible, and that the connection is as firm as possible under the circumstances.

I claim:

1. A prophylactic article of the class described, comprising a tubular body of flexible material, a cap and communicating reservoir member of like material, said cap and reservoir spaced from the tubular body to provide an open area therebetween, said cap forming means for covering only the tip of the glans for maximum exposure of the glans whilst maintaining the position of the reservoir, and means connecting the body and member to retain the maximum open area between the same, whilst maintaining the initial relationship thereof.

2. An article as claimed in claim 1, wherein the means comprise strap-like elements connected at the opposite ends to the respective parts to maintain the same in spaced relation.

3. An article as claimed in claim 2, wherein the body is of open-ended construction, the cap member is of generally hemispherical form with the open end spaced from and opposite the body at one end thereof and the strap-like elements connect the parts.

* * * * *